(12) United States Patent
Hee et al.

(10) Patent No.: US 8,894,207 B2
(45) Date of Patent: Nov. 25, 2014

(54) ENHANCED BIOMETRY USING OPTICAL COHERENCE TOMOGRAPHY

(71) Applicant: Optovue, Inc., Fremont, CA (US)

(72) Inventors: Michael Hee, Burlingame, CA (US); Jay Wei, Fremont, CA (US); Ben Jang, Cupertino, CA (US); Tony Ko, Cupertino, CA (US)

(73) Assignee: Optovue, Inc., Fremont, CA (US)

( * ) Notice: Subject to any disclaimer, the term of this patent is extended or adjusted under 35 U.S.C. 154(b) by 0 days.

(21) Appl. No.: 13/789,283

(22) Filed: Mar. 7, 2013

(65) Prior Publication Data

US 2013/0235343 A1    Sep. 12, 2013

Related U.S. Application Data

(60) Provisional application No. 61/608,047, filed on Mar. 7, 2012.

(51) Int. Cl.
*A61B 3/14* (2006.01)
*A61B 3/00* (2006.01)

(52) U.S. Cl.
USPC .......................... 351/206; 351/246

(58) Field of Classification Search
USPC .................................. 351/200–246
See application file for complete search history.

(56) References Cited

U.S. PATENT DOCUMENTS

| | | | |
|---|---|---|---|
| 5,042,938 A | 8/1991 | Shimozono | |
| 5,258,791 A | 11/1993 | Penney et al. | |
| 5,347,328 A | 9/1994 | Sekine et al. | |
| 6,144,456 A | 11/2000 | Chavanne et al. | |
| 6,231,186 B1 | 5/2001 | Broadus et al. | |
| 6,634,751 B2 | 10/2003 | Turner et al. | |
| 6,806,963 B1 | 10/2004 | Wälti et al. | |
| 7,370,966 B2 | 5/2008 | Fukuma et al. | |
| 7,618,372 B2 | 11/2009 | dela Houssaye | |
| 7,866,821 B2 * | 1/2011 | Ferguson et al. | 351/221 |
| 7,884,946 B2 | 2/2011 | Blalock et al. | |
| 8,033,665 B2 * | 10/2011 | Ferguson et al. | 351/221 |
| 8,049,899 B2 | 11/2011 | Waelti et al. | |
| 8,408,704 B2 * | 4/2013 | Tomidokoro et al. | 351/206 |
| 8,425,036 B2 * | 4/2013 | Yoshida et al. | 351/205 |
| 8,437,008 B2 * | 5/2013 | Fercher et al. | 356/497 |
| 2003/0011745 A1 | 1/2003 | Molebny et al. | |
| 2005/0203422 A1 | 9/2005 | Wei | |
| 2007/0279592 A1 | 12/2007 | Hanebuchi | |
| 2008/0055543 A1 | 3/2008 | Meyer et al. | |
| 2008/0151188 A1 | 6/2008 | Kawai et al. | |
| 2008/0218691 A1 | 9/2008 | Fercher | |
| 2008/0285043 A1 | 11/2008 | Fercher et al. | |

(Continued)

OTHER PUBLICATIONS

Fercher et al., "Eye-length measurement by interferometry with partially coherent light," Optics Letters, vol. 13, No. 3, Mar. 1988, pp. 186-189, 3 pages total.

(Continued)

*Primary Examiner* — Mohammed Hasan
(74) *Attorney, Agent, or Firm* — Haynes & Boone, LLP

(57) ABSTRACT

An imaging method is disclosed. An imaging method according to some embodiments can include obtaining a plurality of measurements of an eye for at least one location by scanning optical radiation across the eye; determining a preferred measurement axis from the plurality of measurements; and processing the plurality of measurements to obtain information of the eye.

21 Claims, 10 Drawing Sheets

(56) References Cited

U.S. PATENT DOCUMENTS

| | | |
|---|---|---|
| 2009/0268209 A1 | 10/2009 | Waeiti et al. |
| 2010/0014051 A1* | 1/2010 | Rathjen .................. 351/206 |
| 2010/0033727 A1 | 2/2010 | Ko et al. |
| 2010/0201946 A1 | 8/2010 | Murakaimi |
| 2010/0271594 A1 | 10/2010 | Bergner et al. |
| 2011/0128499 A1 | 6/2011 | Endo et al. |
| 2011/0149245 A1* | 6/2011 | Barth et al. .................. 351/215 |

OTHER PUBLICATIONS (SRK/T) Retzlaff et al., "Development of the SRK/T intraocular lens implant power calculation formula," Journal Cataract Refract Surgery, vol. 16, pp. 333-340, May 1990, 8 pages total.

(Holladay 1) Holladay et al., "A three-part system for refining intraocular lens power calculations," Journal Cataract Refract Surgery, vol. 14, Jan. 1988, pp. 17-24, 8 pages total.

(HofferQ) Hoffer, Kenneth J. MD, "The Hoffer Q formula: A comparison of theoretic and regression formulas," Journal Cataract Refract Surgery, vol. 19, Nov. 1993 pp. 700-712, 13 pages total.

(Holladay 2) Holladay et al., "Features in the HIC.SOAP Professional and Deluxe Edition," Holladay IOL Consultant Software, retrieved from http://www.hicsoap.com/topic/12-hicsoap-professional-edition.aspx, Aug. 29, 2013, 3 pages.

(Haigis) Haigis et al., "Comparison of immersion ultrasound biometry and partial coherence interferometry for intraocular lens calculation according to Haigis," Graefe's Arch Clin Exp Ophthalmol, 2000; 238; 765-773, 9 pages total, Aug. 2000.

International Search Report and Written Opinion mailed May 20, 2013 in International Application No. PCT/US2013/029703, 9 pages.

* cited by examiner

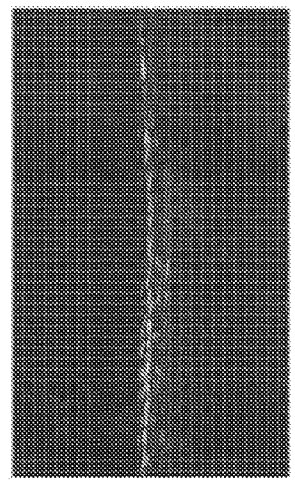
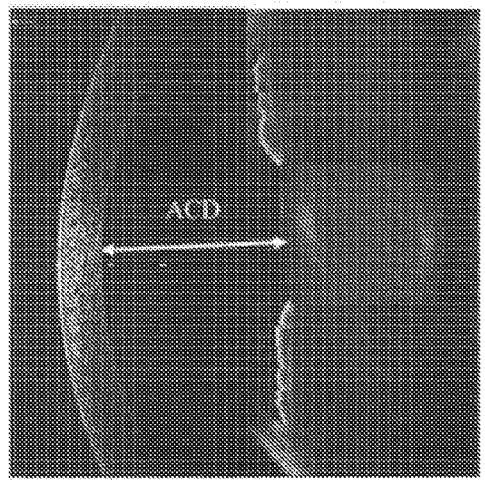
FIG. 6B
Fig. 6A
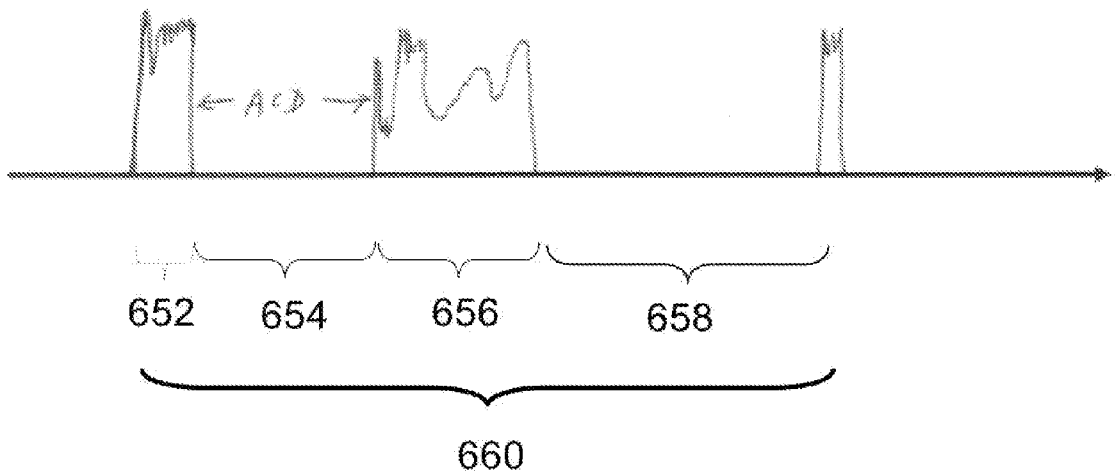
FIG 6C

ENHANCED BIOMETRY USING OPTICAL COHERENCE TOMOGRAPHY

RELATED APPLICATIONS

This application claims priority to U.S. Provisional Application 61/608,047, filed on Mar. 7, 2012, which is herein incorporated by reference in its entirety.

BACKGROUND

1. Field of the Invention

Embodiments of the present invention relate to a device for optical coherence tomography for determining geometric structures and optical biometry of the eye. In particular, embodiments of the present invention relate to a device for optical coherence tomography for determining the power of an intraocular lens implant and the condition of the retina.

2. Description of Related Art

Modern intraocular lens (IOL) calculation formulas rely on the measurement of several geometric parameters of the eye in order to calculate the power of an implanted intraocular lens after cataract surgery. Third-generation formulas such as the SRK/T (Retzlaff J A, Sanders D R, Kraff M C, "Development of the SRK/T intraocular lens implant power calculation formula" J Cataract Refract Surg 1990; 16:333-340), Holladay 1 (Holladay J, et al., "A 3-part system for refining intraocular lens power calculations" J Cataract Refract Surg 1988; 14:17-24), and HofferQ (Hoffer K J., "The Hoffer Q formula: A comparison of theoretic and regression formulas" J Cataract Refract Surg 1993; 19:700-712.) require measurement of axial eye length and corneal curvature. Fourth-generation formulas such as Holladay 2 (available from Holladay et al., http://www.hicsoap.com/topic/12-hicsoap-professional-edition.aspx) and Haigis (Haigis W, et al., "Comparison of ultrasound biometry and partial coherence interferometry for intraocular lens calculation according to Haigis" Graefe's Arch Clin Exp Ophthalmol 2000; 238; 765-773) also require additional parameters, including anterior chamber depth and lens thickness, which allow for more accurate calculations. These parameters are important for estimating the effective lens position (ELP) of the IOL in the eye.

An ultrasound A-scan may be used to measure axial eye length. However, the results from ultrasonic measurements may be less accurate and less reproducible than optical methods. First, the ultrasonic wavelength is typically longer than the optical wavelength making the ultrasonic measurements less precise. Second, if a contact ultrasonic probe is used, pressure applied to the cornea may distort the axial length measurement. Third, an immersion ultrasonic probe can be uncomfortable for the patient. Finally, it is difficult to accurately place the ultrasound probe on the desired measurement axis of the eye. However, the ultrasonic measurement can often be performed even when there is a dense cataract, which renders measurement using optical methods difficult.

The health of the eye is an important consideration prior to cataract surgery. Current optical biometers only obtain measurements on a single axis of the eye and are therefore unable to create an image of the cornea or retina.

Conventionally, measurements of corneal curvature and axial length are obtained with two different instruments or two different measurement beams. For example, if ultrasound is used to measure the axial eye length, a separate optical keratometer or a topographer are used to measure the corneal curvature. Some devices use optical methods to measure the axial length and corneal curvature. In these methods, partial coherence interferometery is used to measure the axial length and a separate optical keratometer is used to measure the corneal curvature. In other methods, the principle of partial coherence interferometry is used to measure the axial length, but a Scheimpflug image (Scheimplfug T., "Der Photoperspektograph and Seine Anwendung. Photogr" Korresp 1906; 43:516) is used to derive the anterior chamber depth and the lens thickness needed for the IOL calculation. The Scheimpflug principle describes how the image or camera plane, lens plane, and object planes of an optical system can be oriented such that the object plane is completely in focus at any depth.

The traditional third and fourth generation IOL formulas assume a fixed ratio between the curvature of the anterior and posterior surfaces of the cornea. Only a measurement of corneal anterior curvature is therefore required to compute corneal refractive power and IOL implant power after cataract surgery. However, in unusual eyes or eyes that have undergone refractive surgery, the relationship between the anterior and posterior corneal surfaces is likely to be altered and the assumptions of the traditional IOL calculation formulas become invalid.

Therefore, there is a need for methods and apparatus to perform biometry measurements.

SUMMARY

In accordance with some aspects of the invention, an imaging method is disclosed. An imaging method according to some embodiments can include obtaining a plurality of measurements of an eye for at least one location by scanning optical radiation across the eye; determining a preferred measurement axis from the plurality of measurements; and processing the plurality of measurements to obtain information of the eye.

In some embodiments, an apparatus includes a scanner for scanning optical radiations across an eye to acquire measurements from at least one surface and at least one internal structure of the eye simultaneously; a lens for focusing the optical radiations on the surface of the eye; a negative power lens for focusing the optical radiation on an internal structure of the eye; and a processor to generate at least one image from the plurality of measurements.

These and other embodiments are further discussed below with respect to the following figures.

BRIEF DESCRIPTION OF THE DRAWINGS

FIGS. 6A, 6B, and 6C show exemplary images of the cornea, the retina, and the cross-sectional measurements using the optical arrangement in FIG. 5, respectively.

DETAILED DESCRIPTION

Figure 1:
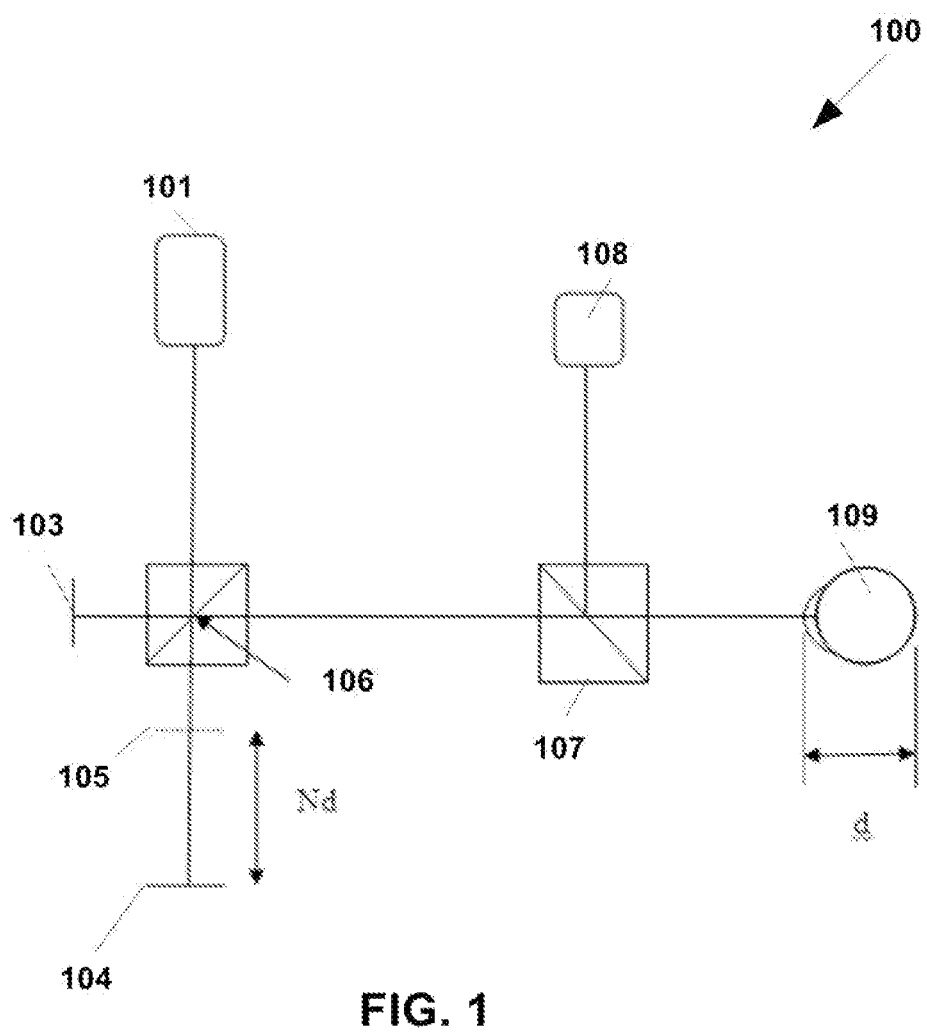
FIG. 1 illustrates a schematic of an optical biometer based on partial coherence interferometry.

Various embodiments of the present invention are described below with reference to the accompanying drawings. It is understood that figures have been simplified for the purposes of explanation herein while leaving out elements which are conventional in the art.

Optical methods of axial eye measurement described below can provide a high precision measurement because the wavelength of light is smaller than the ultrasonic wavelength. Measurements using optical methods can also be obtained without contact with the eye. In addition, the user may be able to manually align the optical measurement beam to the desired optical axis of the eye by monitoring the specular reflection of light from the cornea.

In some embodiments, the optical biometry can be improved by utilizing a plurality of measurements acquired at a plurality of transverse locations across the eye. In some embodiments, an apparatus that can couple an optical biometer to a beam scanning mechanism and a method utilizing the plurality of measurements to obtain the desired geometric properties of the eye with better accuracy and improved ease-of-use, especially under the conditions of dense cataract or poor user alignment on a preferred measurement axis of the eye, can be provided.

In some embodiments, a method that uses the optical reflections from the cornea obtained from the plurality of measurements to locate the desired optical axis of the eye, such as, the cornea vertex normal can be performed. With this method, a measurement of axial length coinciding with the cornea vertex normal can be selected from the plurality of measurements, even if the instrument is not perfectly centered on the cornea vertex normal.

In some embodiments, an apparatus for forming a simultaneous optical image of the cornea and retina can include a lens to focus optical radiation on the cornea, and a negative lens to simultaneously focus the optical radiation on the retina. In some embodiments, the apparatus allows a measurement of axial eye length to be performed from the simultaneous optical reflections from both the corneal and retinal surfaces. The apparatus can also provide simultaneous optical images of the retina and cornea capable for evaluating the health of the eye prior to considering any surgical intervention, such as a cataract surgery.

In some embodiments, a method for using the plurality of measurements to improve measurement accuracy through dense cataracts or cataracts with focal opacity can be performed. In some embodiments, an array of measurements may be obtained at different transverse locations so that at least some measurements would avoid the focal opacity. The locations of the measurements may be spaced closely enough to avoid the influence by retinal curvature and to permit averaging of the optical signal from the retina to enhance penetration through a dense cataract. The position of the apex of the cornea can be located from the plurality of measurements by means of peak detection or curve fitting.

In some embodiments, a method for using the plurality of measurements to define the curvature of the anterior cornea, the curvature of the posterior cornea, the anterior chamber depth, and the lens thickness, which are additional parameters that are important for intraocular lens power calculation, can be performed. These measurements can be obtained with a single measurement beam in a single device.

Methods of using low-coherence or partial coherence interferometry to measure axial eye length are disclosed. There are two commercial instruments that use the technique of partial coherence interferometry to measure the geometric properties of the eye. The IOLMaster (Carl Zeiss Meditec, USA) measures the interference signal between the corneal reflection and the retinal reflection to provide a measurement of axial eye length. This measurement is relatively insensitive to the longitudinal distance between the cornea and the instrument because the detected interference signal only depends on the relative distance between the cornea and retina. However, the user must manually adjust the horizontal and vertical position of the instrument itself in two transverse dimensions along the desired measurement axis of the eye for alignment. Accurate manual alignment can be difficult to achieve in eyes with poor fixation or poor cooperation from the patient. In clinical practice, this method requires the anterior chamber depth and lens thickness to be obtained separately from a video image of an off-axis slit-beam incident on the cornea, iris and lens; this separate method provides measurements that are less accurate than measurements that could otherwise be obtained using an interferometric method.

According to some embodiments of the present invention, measurements for both the anterior chamber depth and lens thickness using interferometric method can be utilized. In addition, corneal curvature, axial length, and lens thickness, can be measured with a single measurement beam in a single instrument.

The Lenstar (Haag Streit, Switzerland) is another instrument that employs time-domain low coherence interferometry to measure the geometric properties of the eye. The Lenstar measures the interference signal formed between the reflective boundaries within the eye and a reference optical path of varying length. The use of a reference optical path allows a measurement of the corneal thickness, the anterior chamber depth, the lens thickness, and the axial length to be obtained simultaneously. However, the user manually aligns the instrument in 3 dimensions with respect to the location of the cornea to obtain an absolute reference of the optical path distance, which is likely to be less accurate in eyes with poor fixation or poor cooperation from the patient.

According to some embodiments of the present invention, a plurality of measurements at different optical axes is obtained, allowing automatic selection or reconstruction of the desired measurement post processing with less measurement error due to user input or manual alignment. In addition, the plurality of measurements obtained by some embodiments may be constructed into an image of the cornea and retina. An optical apparatus is disclosed herein that allows simultaneous imaging of the cornea and retina.

A common disadvantage of previous optical methods used for measuring the axial eye length is that the optical beam usually employed cannot penetrate a very dense cataract, which causes significant light scattering. A method was proposed to solve this problem by increasing the measurement time to enable measurements through a dense cataract. In some instances, the area of the strongest light scattering may be localized to a particular portion of the lens. This condition may be more likely to occur with an anterior polar, posterior polar, posterior subcapsular, or focal anterior cortical cataract. In these cases, an optical measurement of axial eye length could possibly be obtained if the instrument were aligned on a preferred measurement axis of the eye which avoided the dense lens opacity. Manually locating the preferred measurement axis in this situation adds difficulty for the operator.

In some embodiments of the present invention, a plurality of measurements on multiple measurement axes is acquired so that at least one light beam could avoid the dense lens opacity and produce useful measurements.

Additionally, some embodiments of the present invention are able to measure both the anterior and posterior corneal curvatures simultaneously with a single measurement beam, allowing a more accurate calculation of the net corneal power after refractive surgery. As discussed below, optical measurements can be obtained using low-coherence interferometry, partial coherence interferometry, or optical coherence tomography.

FIG. 1 shows the optical layout of a dual beam interferometer 100 with partially coherent light. A measurement of axial eye length is performed along a single measurement axis of the eye 109 at a time. In some embodiments, a scanning mechanism (not shown) can be included to obtain a plurality of measurements over an area of eye 109. As shown in FIG. 1, a light source 101 with a short coherence length provides light to a beam splitter 106. The light is split into a path incident on mirror 103 and a path incident on mirror 104. These two light paths are recombined at beamsplitter 106 and incident onto the eye 109 where it is reflected from both the cornea and retina. After reflection from beamsplitter 107, an interference signal appears at detector 108 when the axial eye length d matches the difference in optical path length Nd between the location of mirror 104 and the equivalent distance 105 as that to mirror 103, shown as a dashed line.

Figure 2A:
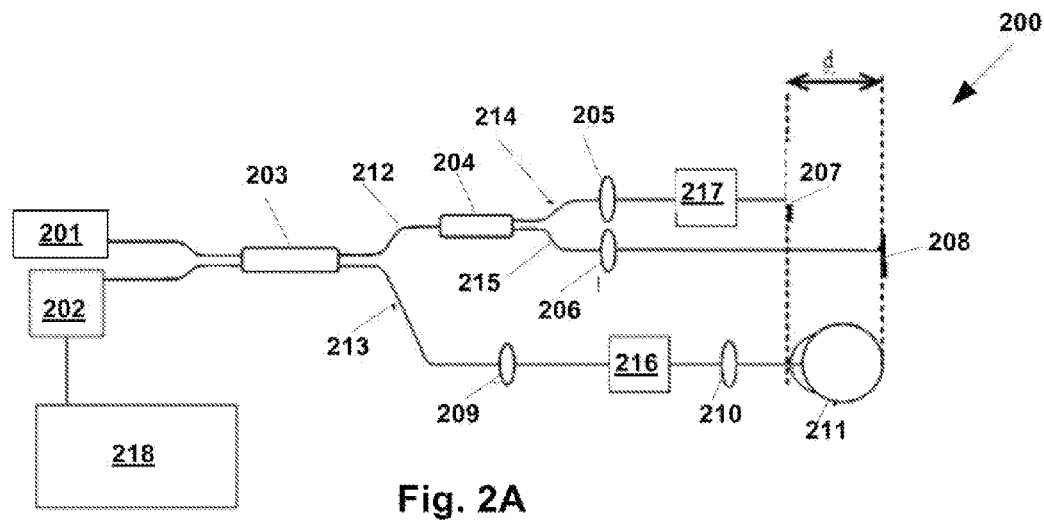
FIG. 2A illustrates an optical coherence tomography system used for simultaneously imaging the cornea and the retina.

FIG. 2A shows the optical layout of an extended range OCT that incorporates two reference arms and a phase generator in one of the references arms to create a full range Fourier domain interferometer that is capable of measuring the eye length. As shown in FIG. 2A, OCT apparatus 200 includes a light source 201 coupled to provide light to a splitter/coupler 203. Splitter/coupler 203 receives light from optical source 201 and sends the energy into both sample arm 213 and reference arm 212. Sample arm 213 may include various collimating lenses 209 and focusing lenses 210. Additionally, sample arm 213 includes a beam scanning mechanism 216 to direct the beam to perform two- or three-dimension transverse beam scanning and imaging of a sample 211. For achieving simultaneous imaging, reference arm 212 includes an additional splitter/coupler 204 that separates the beam of light received from splitter/coupler 203 into two or more reference arm paths, such as reference path 214 and reference path 215. Reference path 214 includes collimating lenses 205 and mirror 207. Reference path 215 includes collimating lenses 206 and mirror 208. Collimator lenses 205 and 206 in reference paths 214 and 215, respectively, collimate the beam from an optical fiber coupled to splitter/coupler 204 and focuses the beams back into the optical fiber after it is reflected from reference mirrors 207 and 208, respectively.

In some embodiments, reference mirror 207 is adjusted to correspond to the anterior segment of the eye while reference mirror 208 is adjusted to correspond to the posterior segment of the eye. The beams returning from the sample arm 213 and reference arm 212 are combined in splitter/coupler 203 and transmitted to detection system 202. The detected signal can then be sent to a processor 218. Phase generator 217 allows the processor 218 to distinguish the signals returning from the anterior and posterior eye. In some embodiment of the present invention, a transverse beam scanning mechanism 216 is included in this configuration to allow a plurality of measurements to be obtained along varying optical axes of the eye. Scanning mechanisms that can be used for scanner 216 or in other measurement techniques can include, for example, mirror that is tilted using a galvanometer or microelectromechanical (MEMS) device, an acousto-optic modulator, a variable diffraction grating, or other mechanical translation of the beam incident on eye 109.

Processor 218 can be, for example, a computer system including one or more processors, internal memory, data storage facilities, and user interfaces. Processor 218 is capable of storing the received image, displaying the image, and analyzing the image according to instructions as described further below.

Figure 2B:
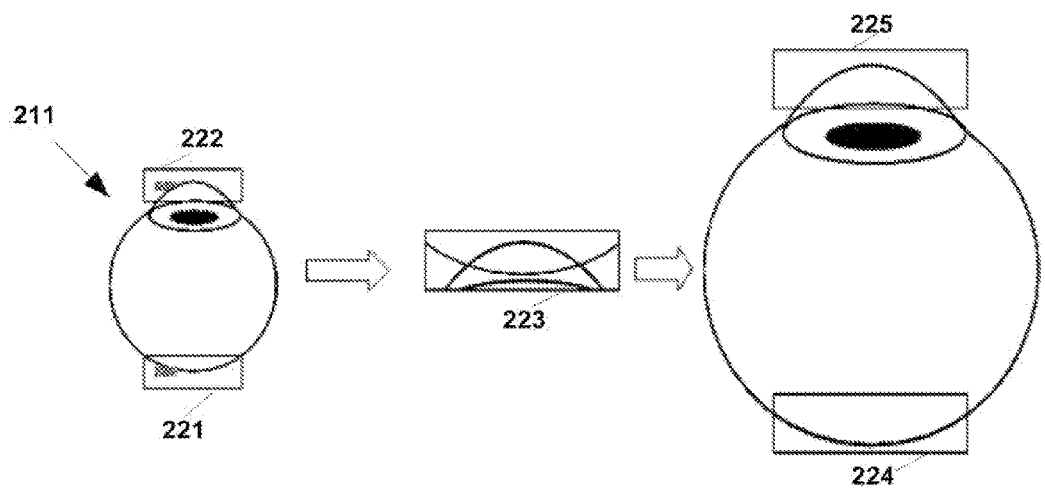
FIG. 2B illustrates images of the cornea and the retina simultaneously acquired using the system shown in FIG. 2A.

FIG. 2B shows an example imaging technique using apparatus 200 as illustrated in FIG. 2A. In FIG. 2B, imaging regions 221 and 222 are of interest in eye 211. The optical path in two reference mirrors can be adjusted such that one reference mirror images the front part of the anterior chamber while the second reference mirror images the retina in the posterior segment of the eye 211. The anterior and posterior eye images will be a superimposed image 223, but can be separated to the anterior chamber image 225 and posterior segment image 224, by the processing unit using the phase information provided by the phase generator 217.

Figure 3A:
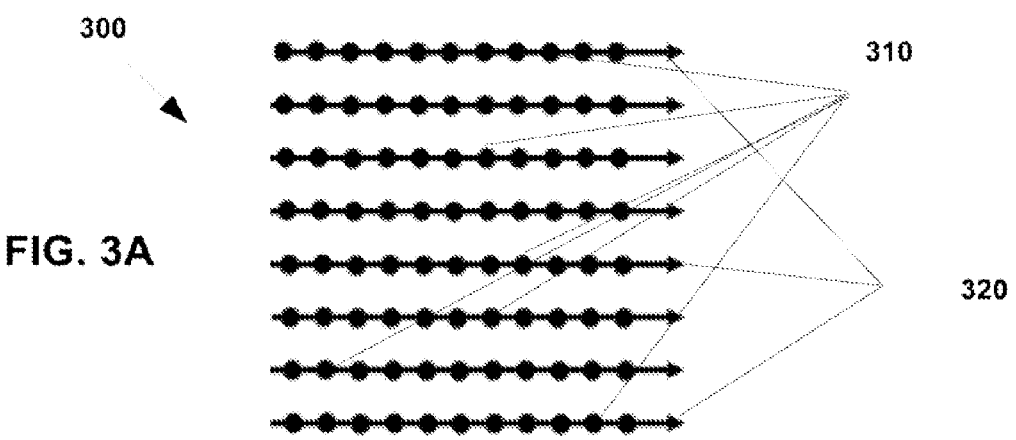
FIG. 3A shows an exemplary volume scan pattern in accordance with some embodiments.
Figure 3B:
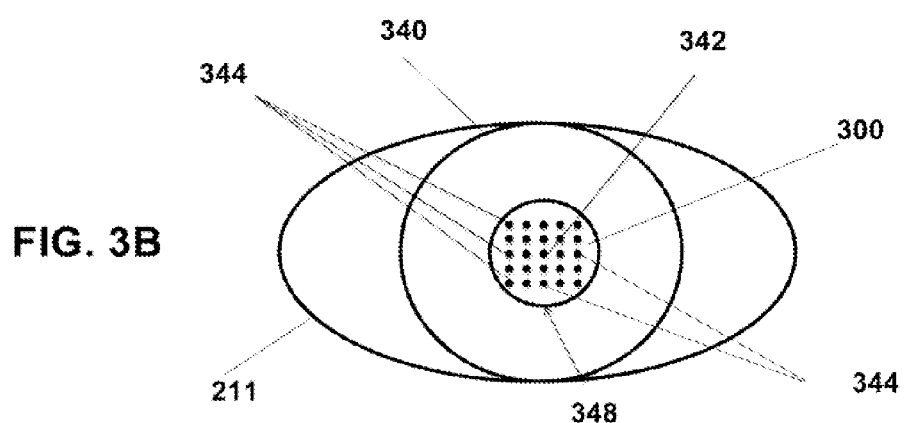
FIG. 3B shows the same scan pattern illustrated in FIG. 3A superimposed onto an eye with good fixation.
Figure 3C:
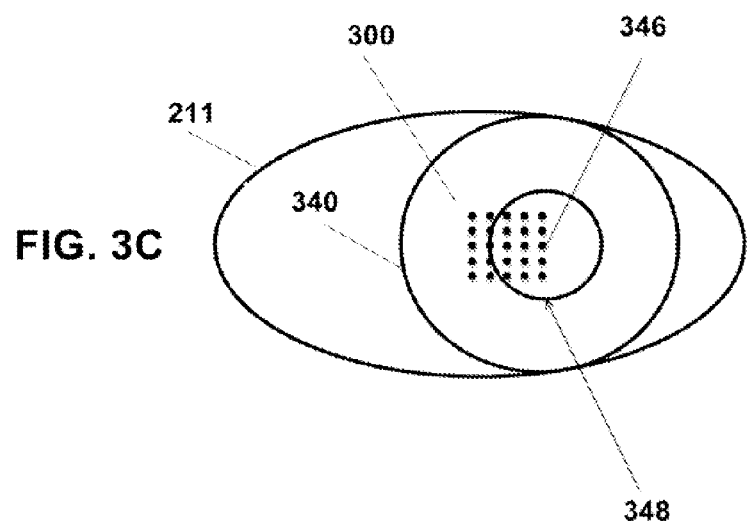
FIG. 3C shows the same scan pattern illustrated in FIG. 3A superimposed onto an eye with poor fixation.

FIGS. 3A, 3B, and 3C disclose a scan pattern for obtaining the plurality of axial eye measurements according to some embodiments of the present invention. In FIG. 3A, the measurement beams are scanned in a 2 dimensional array 300 in the x-y plane with the measurement beam going into the page in the z-direction indicated by dots 310. Each dot 310 represents an A-scan, and the combination of A-scans produces a 3 dimensional volume of geometric measurements covered by the scan array 300. The scan beams 310 can be arranged in alternate configurations, such as an unequally spaced mesh. In some embodiments, the scanning can follow the scan direction 320 to obtain the 3D data volume. The array of measurements 300 is advantageous over other biometry methods because multiple measurements at different locations can be obtained within a single scan.

One advantage of the plurality of measurements 300 over the prior art is that as long as the entire array is positioned approximately over the desired measurement axis of the eye, there is increased probability that at least one measurement beam will be coincident or approximately coincident with the preferred measurement axis, which can be the cornea vertex normal or the corneal apex, or center of the pupil. As is customary in the art, axial eye length measurement is usually acquired along the eye's direction of fixation or the direction of sight. In other methods, the optical biometer might be further aligned by the operator until a specular reflection from the cornea is located, which defines the cornea vertex normal. In situations with uncooperative patients, or patients with dense cataract, or corneal or retinal disease, it may be difficult for the operator to locate the corneal vertex normal accurately due to excessive eye motion or poor fixation. An inexperienced operator may also have more difficulty performing proper alignment. The rapid acquisition of the array of measurements 300 according to some embodiments of the present invention increases the probability that at least one of the measurements is exactly or approximately coincident with the preferred measurement axis, customarily the cornea vertex normal.

There are several methods whereby the preferred measurement axis may be determined from a plurality of corneal measurements. In some embodiments, the preferred measurement axis may be directly selected from the plurality of measurements using criteria such as location information with respect to the pupil. The axial location of the cornea can then be selected to correspond to the corneal reflection on the preferred measurement axis.

Figure 9:
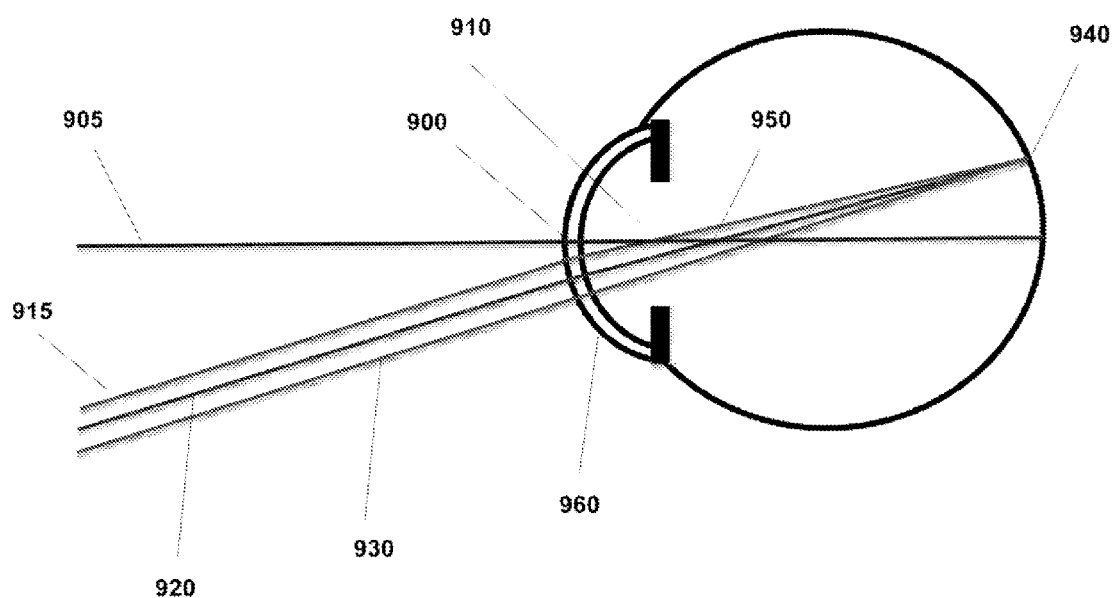
FIG. 9 shows a pictorial representation of an eye with different measurement axes.

FIG. 9 shows a variety of possible measurement axes such as the pupillary axis (optical axis) 905, the line-of-sight 915, the visual axis 920, or the corneal vertex normal 930. The pupillary axis 905 is defined by a ray passing perpendicularly through the center of the pupil 910. The line-of-sight is defined by a ray which passes through the center of the pupil 910 and reaches the fovea 940. The visual axis 920 is a straight line passing through the eye's optical nodal point 950 and intersecting the fovea 940. The corneal vertex normal 930 is defined by a ray which intersects the fovea 940 and is perpendicular to the curve of the anterior cornea 960.

A preferred measurement axis or axial distance to the cornea can be determined by a function of the corneal reflections using all or some of the plurality of measurements. For example, the location of the corneal reflection along the preferred measurement axis can be located by user review of the individual measurements, or be automatically or semi-automatically determined by a processing unit. In some embodiments, the processing unit may evaluate the plurality of measurements to identify the measurement with the strongest corneal reflection, typically occurring at the corneal vertex normal 930, as indicative of the preferred measurement axis. Optical measurements acquired along a measurement axis close to the corneal vertex normal 930 often produce a stronger reflection than measurements from other locations due the more normal incidence of the measurement beam onto the curved corneal surface. In some embodiments, the corneal apex 900, the highest point of the cornea having the largest mean curvature, may be identified by applying a curve fitting to a subset or to all of the measurements, in 2 or 3 dimensions. In other embodiments, an average, or median, or other statistical function of the corneal measurements may be used to identify this location as the preferred measurement axis. Other methods of identifying the location of the corneal reflection will be apparent to those skilled in the art using the plurality of the measurement disclosed herein. It is also apparent that these methods may apply equivalently to other possible preferred measurement axes, such as an optical axis defined by the line-of-sight, the pupillary axis, or the visual axis.

FIG. 3B illustrates application of data array 300 onto an eye 211. Eye 211 includes cornea 340 with pupil 348. As shown in FIG. 3B, the A-scans of data array 300 are within pupil 348. The preferred measurement axis may be selected from the plurality of measurement axes, such as the pupillary axis 905, the line-of-sight 915, the visual axis 920, or the cornea vertex normal 930. Measurement axis 342 in FIG. 3B corresponds to the line-of-sight axis 905. In FIG. 3C, the A-scans of data array 300 only partially overlap the pupil due to either eye motion, poor patient fixation, or improper instrument alignment. However, a measurement 346 along the line-of-sight axis 905 may still be obtained from the data array 300.

The relationship between the transverse dimensions of the array of measurements 300 and the curvature of cornea 340 further influences the identification of the preferred measurement axis. The average radius of curvature of cornea 340 is approximately r=7.6 mm and therefore the axial position z of a given corneal reflection can vary by approximately $\Delta z \approx h^2/(2r)$ from the corneal apex to a peripheral location on cornea 340, where h denotes the radial distance from the corneal apex to the peripheral location.

In some embodiments, an average, or median, or other evaluation of the corneal measurements may be used to identify the optimal corneal location. In normal eyes, the intraocular lens (IOL) power is approximately related to the axial length by a factor of 2.5 (2.5×axial length in mm); that is, a 30 micron variability in axial length is equivalent to about a 0.08 diopter (D) variation in IOL power. Currently, IOLs are usually available in 0.5 increments, although some are available in 0.25 D increments. Therefore, a less than 30 micron variability in axial length measurement is not clinically significant in the choice of IOL implant power after cataract surgery. For example, as shown in FIG. 3B, if the array of measurements 300 spans a linear distance of 1 mm diameter centered on the line-of-sight 342 of an average human cornea 340, the location of the most peripheral measurement 344 along the x and y axis will be approximately $\Delta z \approx (0.5 \text{ mm})^2/(2 \cdot 7.6 \text{ mm})=16$ microns closer to the retina in the z-direction than the location from the central measurement taken at the line-of-sight 342. Since the variation in the entire 1 mm×1 mm array of locations in array 300 has negligible effect on the clinical use of the calculated IOL power, the array of measurements 300 of the corneal surface can be averaged to estimate the axial length. However, if for example, the array of measurements spans a 2 mm diameter on the cornea, the variation in the location of the corneal surface will be increased to approximately 65 microns. Obtaining the axial length using the average corneal measurements may have more influence on an IOL calculation. In this case, a curve-fitting or peak detection process can be used to identify the corneal measurement closest to the vertex normal, which would also be the measurement that produces the longest axial length. For the reasons stated above, differences in patient motion and operator training render inconsistent and inaccurate measurement location. In accordance with some embodiments of the present invention, the additional measurement data obtained using the array of measurement 300 provide flexibility to select and/or process multiple measurements to estimate the best corneal measurement.

The plurality of A-scan measurements also improves the accuracy in identifying the retinal reflection. The short optical wavelength used in optical method leads to measurement with higher axial resolution; optical biometry method commonly known in the art can distinguish multiple retinal reflections, including reflections from the inner surface of the retina and the retinal pigment epithelium (RPE). Any of these measurements may be used to locate the position of the retina in order to determine the axial eye length.

The preferred measurement axis often intersects the center of the fovea as this is the retinal location responsible for the greatest visual acuity. In patients with macular disease, such as geographic atrophy, myopic degeneration and staphyloma, macular hole, the patient may have difficulty fixating on an alignment light which is generally coincident with the measurement beam. FIG. 3C shows an example of the array of measurements 300 used in a patient with poor fixation. Here, a plurality of measurements 300 is acquired at different transverse locations across the retina and the array of measurements 300 is used to increase the probability of obtaining a measurement through the preferred measurement axis. In the example illustrated in FIG. 3C, the measurement closest to or impinging on the fovea may be selected for further measurement analysis and calculations. In FIG. 3C, beam 346 is the beam location most closely corresponding to the preferred measurement axis.

Figure 4A:
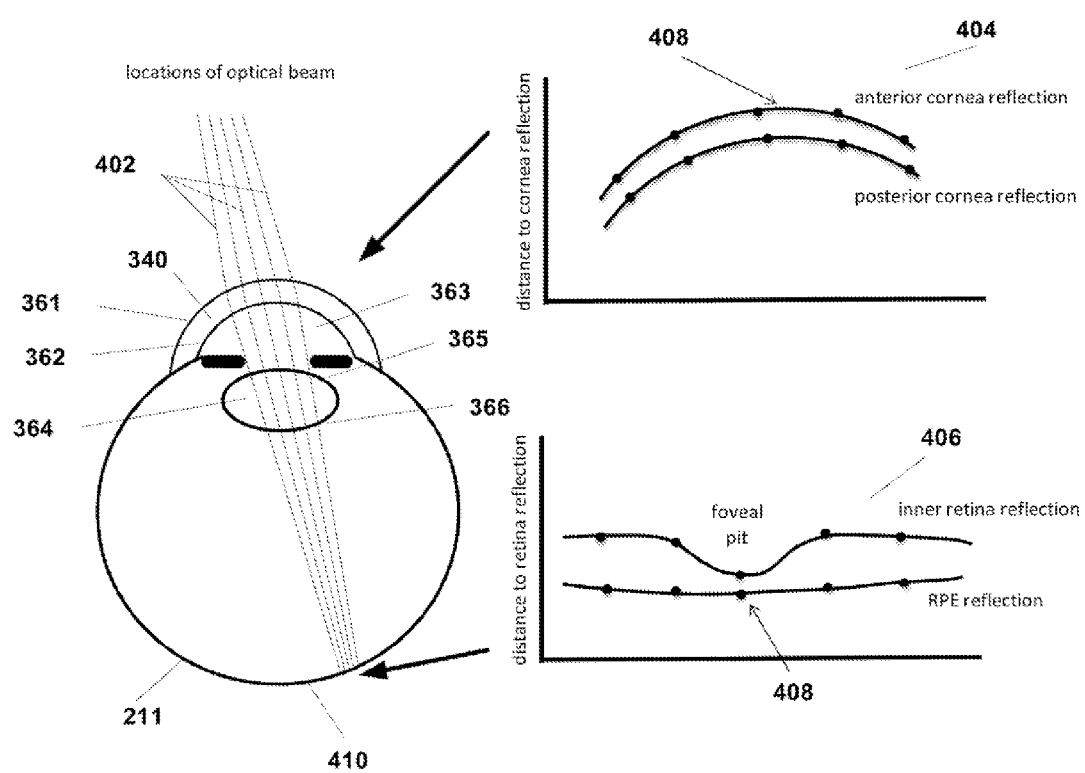
FIG. 4A shows example measurements of a normal eye.

FIG. 4A show an exemplary cross-section of eye 211 with a plurality of optical beams 402 going through a normal eye and impinge onto the fovea 410. The plurality of measurements provide data for further analysis and processing for both the anterior and the posterior segments, as illustrated in data plots 404 and 406 illustrated in FIG. 4A. Plot 404 illustrates the array data 300 as a function of distance to cornea reflection for both anterior cornea reflection and posterior cornea reflection from cornea 340. Plot 406 illustrates the array data 300 as a function of distance to retina reflection for the inner retinal reflection and RPE reflection of retina 410. Since the preferred measurement axis often intersects the center of the fovea, in patients with fixation difficulty, the image of the fovea can be used in some embodiments of the present invention to determine the preferred measurement axis 408.

Figure 4B:
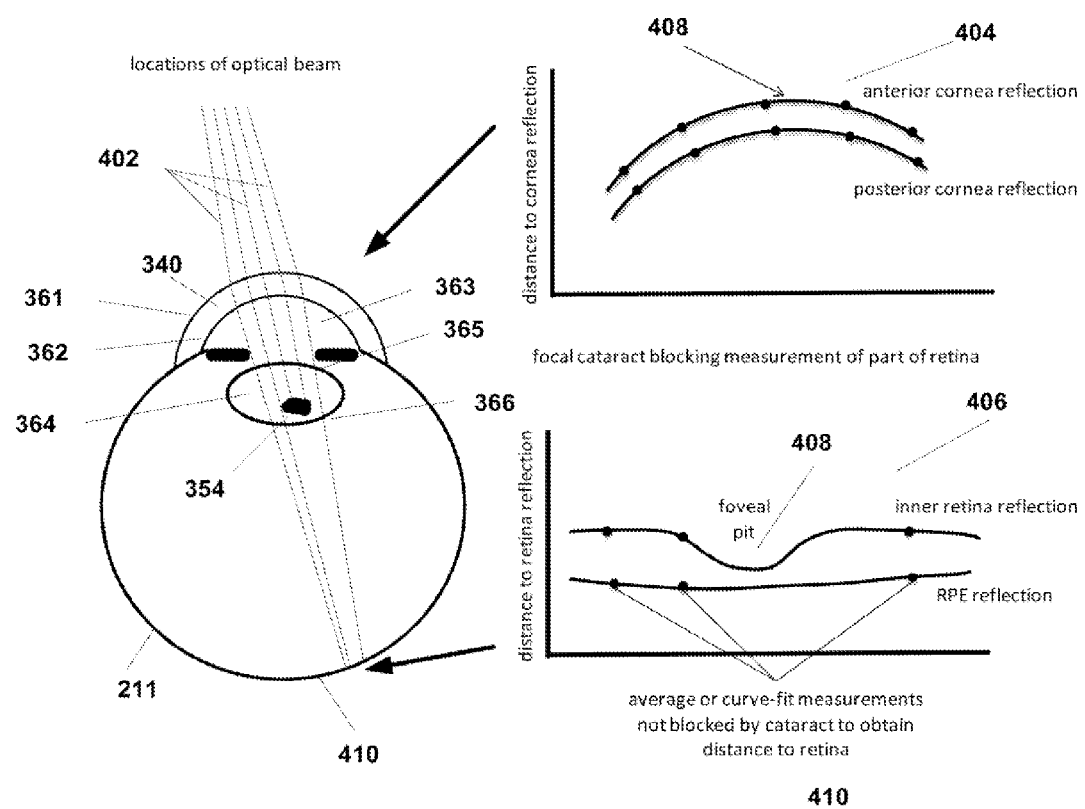
FIG. 4B shows example measurements of an eye with a cataract.

Some methods according to embodiments of the present invention may also have advantages over previously proposed solutions in identifying the retinal reflection in the presence of a dense cataract or a cataract with a dense focal opacity. A dense focal lens opacity, such as opacity 354 in FIG. 4B, may be especially apparent in some cases of an anterior polar, posterior polar, posterior subcapsular, or anterior cortical cataract. In the presence of a dense focal opacity, automatically obtaining a plurality of measurements at varying transverse locations may allow one or several measurements to be performed through a region of the cataract which is less dense. FIG. 4B illustrates an example of such processing. In some embodiments of the present invention, a plurality of measurements can be acquired using the scan array 300 to avoid a focal opacity 354 which improves upon the prior art where the user would have to manually re-align the optical biometer to find a less dense region of the cataract. Using the plurality of measurements, the user can then select the strongest retinal reflection or to perform further processing in order to compute the location of the retina. Alternatively, a function of the plurality of retinal measurements such as averaging or curve fitting may be employed to determine the retinal location.

In the presence of a uniformly dense cataract, the optical reflections from the retina will be weak, and the plurality of measurements at varying transverse locations allows the retinal reflection to be more accurately determined from a function based on the plurality of measurements, rather than just a measurement taken from a single retinal location. For example, the strongest retinal reflection from the plurality of retinal reflections may be selected. Alternatively, the plurality of retinal reflections may be averaged. In this manner, the visibility of the average reflection can be enhanced in the presence of noise, which is reduced by the averaging.

The ability to perform averaging on measurements of the retina might be affected by the curvature of the retina 410 and the transverse extent of the measurement volume. The radius of curvature of the retina 410 in normal eyes is approximately 13.4 mm and is larger than the radius of curvature of the cornea 340. A maximum transverse displacement of the A-scan of 0.5 mm on the retina allows the plurality of measurements to be acquired in a 1 mm×1 mm volume and only an estimated $\Delta z \approx h^2/(2r) = 9$ micron variability in the axial position of the retinal reflection. Therefore, if the scanning volume is relatively small (eg. 1 mm×1 mm), the measurements of the retinal reflections can be averaged to obtain measurements in the presence of a dense cataract opacity 354 without significantly affecting the measurement precision. For significantly larger measurement volumes, the radius of curvature of the retina 410 might be more significant. In this case, alternative processing methods, such as curve fitting, can be used to derive the optimal retinal location from the plurality of retinal locations, as illustrated in the plots in FIG. 4B. Applying curve fitting to multiple retinal measurements will have an effect similar to averaging because measurement noise which strongly affects a single measurement will have a substantially weaker effect on the position of a curve determined by multiple measurements.

The method of automatically obtaining a plurality of biometer measurements at separate transverse locations also improves on the prior art by improving on the ability to evaluate the health of the eye, which is important in the consideration of whether or not to proceed with cataract surgery. In some embodiments, the pattern of transverse measurement locations can be a regularly spaced two-dimensional array 300. The array of measurements comprising the depth of reflections from structures on the surface or within the eye may be combined and displayed as a two-dimensional cross-sectional image, or a three-dimensional volume of eye structures. For example, the presence of retinal abnormalities, such as epiretinal membrane, macular edema, or other pathology, may be determined from a cross-sectional image and can provide valuable information in evaluating the visual potential of an eye about to undergo cataract surgery. In the presence of normal retinal anatomy, the location of the fovea can be accurately identified based on its characteristic morphological features, such as the foveal depression/pit which is related to the lack of retinal nerve fiber layer, inner plexiform layer and inner nuclear layer in the region. In a similar manner, cross-sectional or volume images of the cornea, anterior chamber, or lens may also be obtained with a single optical biometer.

It will be evident to practitioners skilled in the art that any method of beam scanning or translation may be used to obtain the plurality of measurements at different transverse locations. Methods of beam scanning includes, but are not limited to, mechanically tilting a mirror using a galvanometer or microelectromechanical (MEMS) device, employing an acousto-optic modulator or variable diffraction grating, or mechanically translating the beam light source or an optical element in the beam path. Alternatively, multiple measurement beams may be employed either simultaneously or in succession to achieve the same purpose of obtaining measurements at varying transverse locations.

Figure 5:
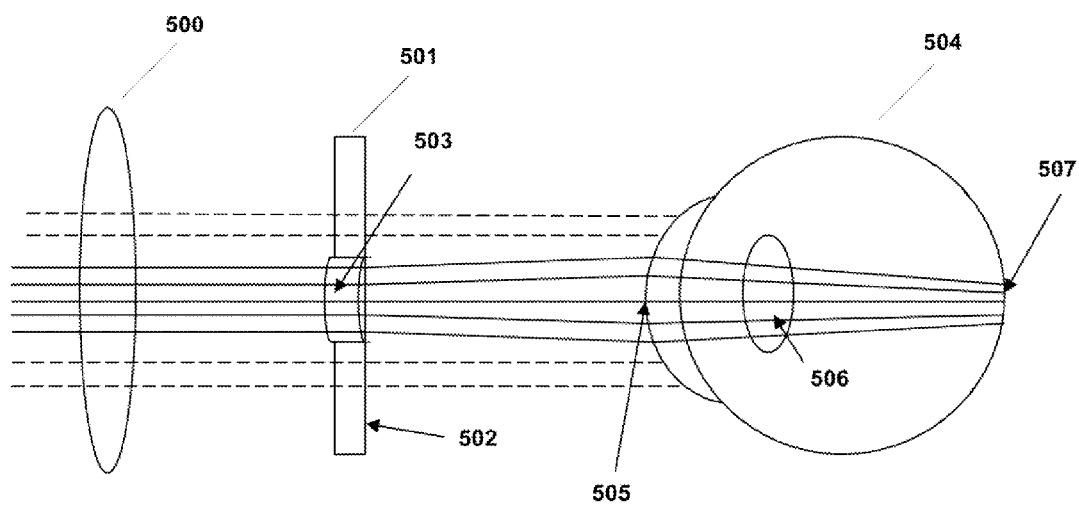
FIG. 5 illustrates an exemplary optical layout to obtain a simultaneous reflection from the cornea and the retina according to some embodiments.

FIG. 5 illustrates an exemplary optical layout according to some embodiments to simultaneously image the cornea and the retina with a wide field-of-view. The optical beam exits from a focusing lens 500 onto a bifocal lens 501. The bifocal lens is composed of a central negative lens element 503 which collimates the focused beam (solid line) before it is incident on the corneal surface 505. The beam is then focused by the eye 504 onto the retina 507. The peripheral zone 502 of the bifocal lens 501 is a flat optical surface. This surface does not change the beam (dotted line) emerging from the focusing lens, and the beam remains focused onto the cornea. In this optical arrangement, the beam is simultaneously focused on the central retina and the paracentral cornea. Therefore, simultaneous measurements of the corneal location and the retina location may be performed as shown in FIG. 5. The optical layout in FIG. 5 using the bifocal lens 501 can be incorporated into the imaging apparatus shown in FIG. 2A to obtain simultaneous measurements of the cornea and the retina. In some embodiments, the bifocal lens 510 can be placed between the focusing lens 210 and the object 211 in FIG. 2A, or any other location obvious to a person of reasonable skills in the art.

In FIG. 5, if the bifocal lens 501 is not present, then the beam would remain focused on the cornea at every measurement location and only corneal measurements would be obtained. In this case, the beam would be divergent at the retina 407, and therefore only a very weak, undetectable retinal reflection would be present, even in the absence of cataract 506. Alternatively, if the bifocal lens 501 consists of a single negative lens element 503, then the beam can be focused on the retina 507, but remain collimated at the cornea 505 at every measurement location. A collimated beam can provide a sufficient corneal reflection in the central cornea due to the normal incidence of the measurement light, but the reflections from the paracentral cornea can be weak because the angle of the corneal surface would tend to reflect the measurement light away from the instrument. Therefore, the bifocal lens design provides advantages in the ability to obtain a simultaneous wide field-of-view image of the cornea 505 and retina 507. A wide-field-of-view image of the cornea 505 is important as it allows the operator to visually assess the corneal image and determine whether the optical biometer is approximately aligned along the preferred measurement axis of the eye. Approximate centration of the biometer is achieved when the operator can center the corneal apex in the image formed from the array of corneal measurements. The optimal measurement axis may be derived from the plurality of measurements as described above. In some embodiments, the corneal and retinal measurements are obtained simultaneously so that computation of the axial length will not be influenced by the distance of the optical biometer to the eye 504 or patient movement when performed separately. The bifocal lens 501 in some embodiments provides separate focuses for both the retina 507 and cornea 505. It will be obvious to one of ordinary skill in the art to use any lens combination to produce a central collimated beam and a peripheral focused beam within the scope of this invention.

Current, "third generation" IOL calculation formulas such as the Holladay 1, SRK/T, and HofferQ require measurements of corneal curvature and axial length in order to compute IOL power. As described above, some methods of the present invention for obtaining a plurality of measurements at different transverse locations may also be used to define the curvature of the cornea 505. The curvature of the cornea 505 may be determined by an algorithm which fits a curve to the locations of the corneal reflections obtained from the plurality of measurement axes. Conventionally, corneal curvature measurements are commonly obtained by an integrated keratometer, or a video camera based on the principle of Scheimpflug photography. Some embodiments of the current invention discussed above allow the corneal curvature and the axial length to be obtained simultaneously with one single optical beam.

Using a similar principal of simultaneous acquisition of the anterior and the posterior segments as shown in FIG. 4A according to some embodiments of the present invention, a measurement of posterior corneal curvature and the anterior corneal curvature, together with the axial length, can be obtained simultaneously. The posterior corneal curvature may be determined by an algorithm which fits a curve to the locations of the optical reflections from the posterior cornea at the plurality of measurement axes. Measurement of posterior corneal curvature is important for IOL implant power calculations after refractive surgery, as refractive surgery alters the normal relationship between the anterior corneal and posterior corneal radius of curvature.

Figure 7:
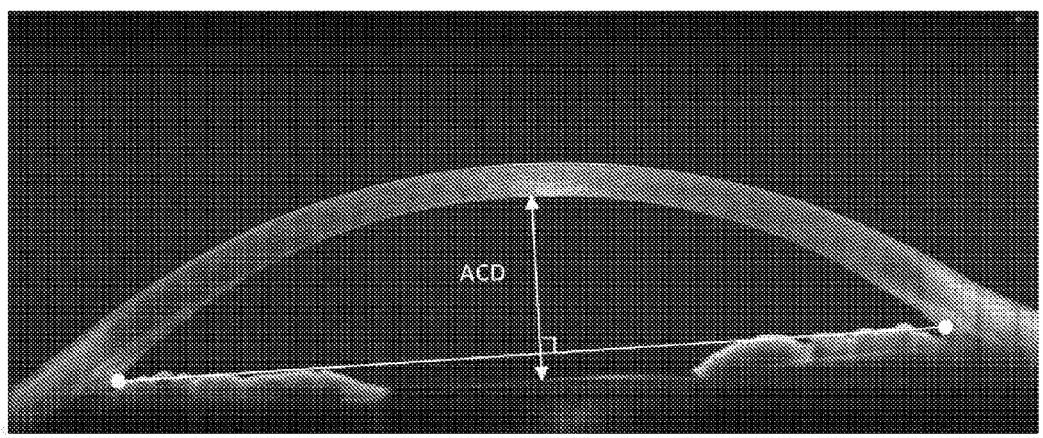
FIG. 7 shows an exemplary image of the cornea according to some embodiments.

"Fourth generation" IOL formulas such as the Haigis or Holladay 2 require additional input parameters, such as the anterior chamber depth and the lens thickness, in order to provide a more accurate IOL power prediction. However, many commonly used optical measurement techniques based on Fourier Domain optical coherence tomography have limited depth range and are unable to image the cornea, the anterior chamber, and the full depth of the lens simultaneously. As shown in FIGS. 6A, 6B, and 6C, the anterior chamber depth and the lens thickness can be determined by two separate measurements obtained with some embodiments disclosed herein. FIG. 6C shows that the lens thickness may be determined by a measurement which includes reflections from the anterior and the posterior lens capsules. The corneal thickness and anterior chamber depth may be determined from a measurement that contains reflections from the anterior cornea and anterior lens capsule, as indicated by ACD in FIG. 7 which is a cross-sectional image of the cornea. The distance between the anterior corneal reflection and fovea may be obtained from a third total axial length measurement as described above. As all measurements are aligned along the preferred measurement axis of the eye (i.e. the cornea vertex normal to the fovea), the measurements may be combined to construct a complete A-scan which specifies the corneal thickness 652, the anterior chamber depth 654, the lens thickness 656, the vitreous length 658, and the total axial length 660, as shown in FIG. 6D.

Figure 8:
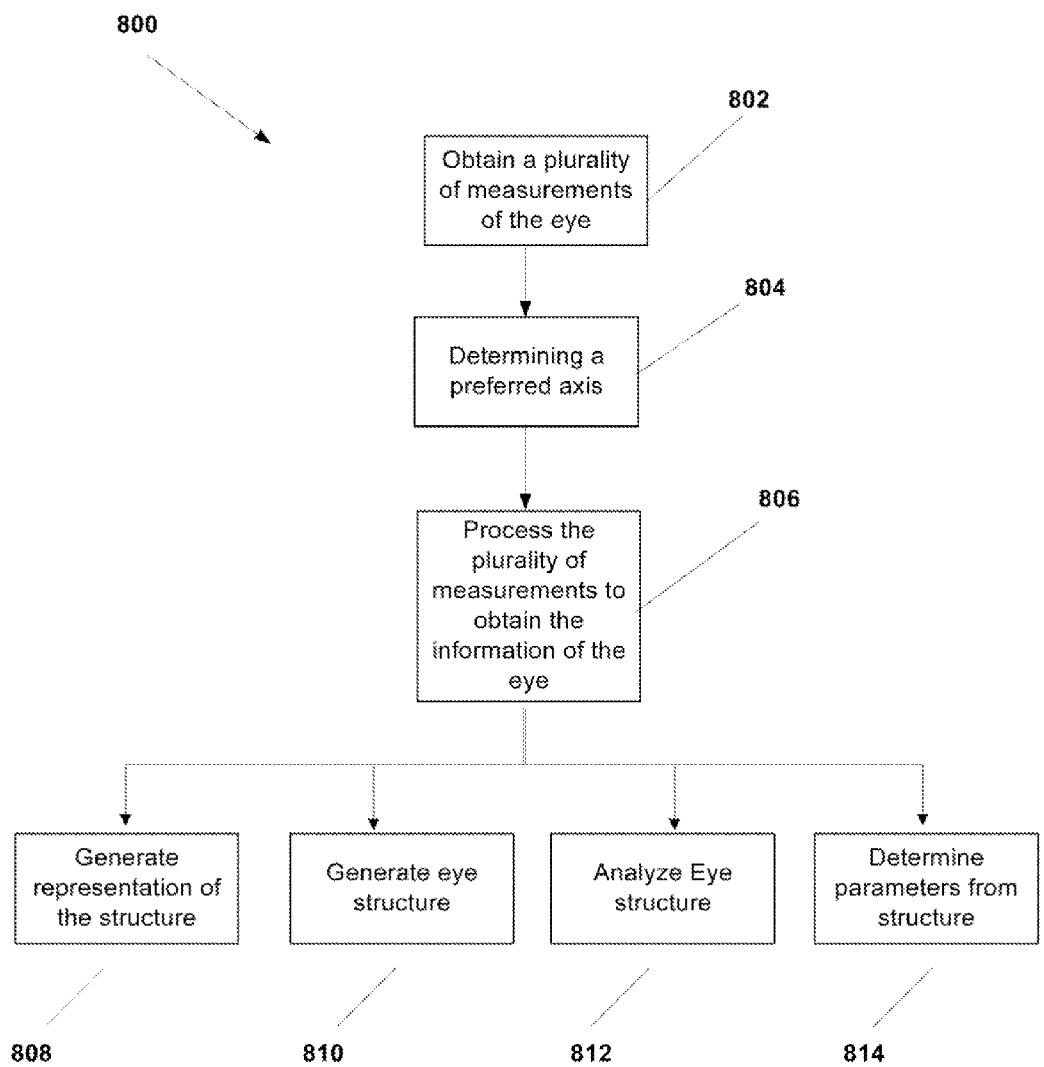
FIG. 8 shows a flowchart of the invention according to some embodiments.

FIG. 8 illustrates an imaging method 800 according to some embodiments of the present invention. In step 802, a plurality of measurements of the eye is obtained. As discussed above, the plurality of measurements can be acquired by techniques such as low-coherence interferometry, partial coherence interferometry, and optical coherence tomography and by imaging apparatus as illustrated in FIGS. 1, 2A and 5.

In step 804, a preferred measurement axis of the eye can be determined. As discussed above, if the preferred measurement axis is the corneal vertex normal, it can be determined by selecting the single measurement from the plurality of measurements which has the largest corneal reflection and also contains a retinal reflection from the fovea.

In step 806, the plurality of measurements can be processed to obtain eye dimensions, such as length, size, and curvature. In some embodiments, step 806 includes step 808, where a 2D or 3D representations of the eye structure is generated. In step 810, the eye structure can be generated based on the 2D or 3D representations. In step 812, the eye structure can be analyzed to determine various features in the eye. In step 814, various parameters of the eye can be determined from images of the various features of the eye determined in step 812.

The representations can include, for example, the cornea 340, the anterior corneal surface 361, the posterior corneal surface 362, the anterior chamber 363, the lens 364, the anterior lens surface 365, the posterior lens surface 366, and the retina 410 (including the anterior retina surface and the posterior retina surface) of the eye by processing the optical reflections from the corresponding regions of the eye. In some embodiments, the cornea vertex normal, visual axis, or a line-of-sight can be determined using the representations. In some embodiments, the fovea of the eye can be determined from the representations by forming an image. In some embodiments, the cornea of the eye can be located and curve fitting can be applied to determine the highest reflection, calculate an average, median, or other statistical functions of the optical reflections of the cornea. Similarly, the retina of the eye can be determined by spatially averaging, curve fitting of the optical reflections from the retina, using the optical reflection from the retina along the axis of the corneal vertex normal, or by selecting the strongest reflection at or near the center of the fovea. The axial length of the eye can be determined by calculating the distance between the location of the cornea and the location of the retina.

Further, corneal thickness can be determined from the eye structure generated by locating the optical reflections from the anterior cornea surface and the posterior cornea surface at or near the vertex normal, spatially averaging or curve fitting the optical reflections from the anterior corneal surface and the posterior corneal surface. By curve fitting, the curvature of the anterior corneal surface can be determined from the optical reflections from the anterior corneal surface. Further, the anterior chamber depth can be determined from the distance between the optical reflections from the anterior corneal surface or the posterior corneal surface and the anterior lens. The thickness of the lens can be determined from the distance between the optical reflections from the anterior lens and the posterior lens. A vitreous thickness of the eye can be determined from the distance between the optical reflections from the posterior lens and the retina. The thickness of the retina can be determined from the distance between the optical reflections from the anterior retina and the posterior retina. The distances to the anterior cornea, the posterior corneal surface, and the retina can be obtained simultaneously. A full-range A-scan can be generated by combining measurements of distance from the anterior corneal surface, the thickness of the cornea, the depth of the anterior chamber, the thickness of the lens and the retina by using the optical reflections from the corresponding regions.

It should be appreciated that alternative and modifications apparent to one of ordinary skills in the art can be applied within the scope of the present inventions. For example, the size, the spacing, the locations and arrangement of the scan array pattern, the lens combinations for wide-field corneal and retinal images can be varied from the specific embodiments disclosed herein.

The invention claimed is:

1. An imaging method, comprising:
    obtaining a plurality of measurements at a plurality of lateral locations across an eye for at least one location by laterally scanning optical radiation across the eye in a scan pattern;
    determining a preferred measurement axis from the plurality of measurements; and
    processing the plurality of measurements to obtain information of the eye along the preferred measurement axis.

2. The method of claim 1, wherein the plurality of measurements is obtained using one or more of low-coherence interferometry, partial coherence interferometry, and optical coherence tomography.

3. The method of claim 1, wherein scanning optical radiation across the eye can be achieved by one or more of tilting a mirror using a galvanometer or microelectromechanical (MEMS) device, operating an acousto-optic modulator, operating a variable diffraction grating, or mechanically translating a light source of the optical radiation.

4. The method of claim 1, wherein the preferred measurement axis can be determined by the amount of optical reflection from a corneal vertex normal.

5. The method of claim 1, wherein the preferred measurement axis can be determined by the optical reflection from a fovea of the eye.

6. The method of claim 1, further generating a 2D or 3D representation of one or more structures of the eye from the plurality of measurements.

7. The method of claim 6, wherein the one or more structures include one or more of a cornea, an anterior corneal surface, a posterior corneal surface, an anterior chamber, a lens, an anterior lens surface, a posterior lens surface, an anterior retina surface, a posterior retina surface, and a retina of the eye.

8. The method of claim 6, further identifying one of a cornea vertex normal, a visual axis, a line-of-sight, an optical axis, a fovea axis as the preferred measurement axis using the plurality of measurements.

9. The method of claim 6, further identifying the fovea of the eye by forming an image from the plurality of measurements.

10. The method of claim 8, further identifying a location of the cornea of the eye by applying a curve fitting to determine the highest reflection of, or calculating an average, a median, or other statistical function of the optical reflections of the cornea.

11. The method of claim 9, further identifying a location of the retina of the eye by spatially averaging, or curve fitting of the optical reflections from the retina, by using the optical reflection from the retina along the axis of the corneal vertex normal, or by selecting the strongest reflection at or near the center of the fovea.

12. The method of claim 6, further determining the axial length of the eye by calculating the distance between the location of a cornea and the location of a retina.

13. The method of claim 6, further determining the corneal thickness.

14. The method of claim 6, further determining the curvature of the anterior corneal surface by curve fitting optical reflections from an anterior corneal surface.

15. The method of claim 6, further determining a curvature of a posterior corneal surface by curve fitting an optical reflection from a posterior corneal surface.

16. The method of claim 6, further determining an anterior chamber depth from the distance between the optical reflections from an anterior corneal surface or a posterior corneal surface and an anterior lens surface.

17. The method of claim 6, further determining a thickness of the lens from a distance between optical reflections from an anterior lens surface and a posterior lens surface.

18. The method of claim 6, further determining a vitreous thickness from a distance between optical reflections from a posterior lens surface and a retina.

19. The method of claim 6, further determining a thickness of a retinal from a distance between optical reflections from an anterior retina and a posterior retina.

20. The method of claim 6, further determining distances to an anterior cornea, a posterior corneal surface, and a retina are obtained simultaneously.

21. The method of claim 6, further generating a full-range A-scan by combining measurements of distance from an anterior corneal surface, a thickness of the cornea, a depth of the anterior chamber, a thickness of the lens and a retina by using the optical reflections from the corresponding regions.

* * * * *